(12) United States Patent
Terry

(10) Patent No.: US 7,879,236 B2
(45) Date of Patent: Feb. 1, 2011

(54) MICRO GAS ATTENDANT SYSTEM

(75) Inventor: Mark Terry, Pocatello, ID (US)

(73) Assignee: Verdure Technologies, Inc., Pocatello, ID (US)

( * ) Notice: Subject to any disclaimer, the term of this patent is extended or adjusted under 35 U.S.C. 154(b) by 171 days.

(21) Appl. No.: 12/248,643

(22) Filed: Oct. 9, 2008

(65) Prior Publication Data

US 2010/0089822 A1 Apr. 15, 2010

(51) Int. Cl.
C02F 3/34 (2006.01)
C02F 3/30 (2006.01)
C02F 11/02 (2006.01)

(52) U.S. Cl. ............... 210/602; 210/603; 210/612; 210/630; 210/903; 210/906

(58) Field of Classification Search .......... 210/602, 210/603, 611, 612, 629, 630, 903, 906
See application file for complete search history.

(56) References Cited

U.S. PATENT DOCUMENTS

| | | | | |
|---|---|---|---|---|
| 4,997,568 | A * | 3/1991 | Vandervelde et al. | 210/603 |
| 5,736,047 | A * | 4/1998 | Ngo | 210/602 |
| 6,032,931 | A * | 3/2000 | Plunkett | 261/77 |
| 6,039,874 | A * | 3/2000 | Teran et al. | 210/605 |
| 6,436,288 | B1 | 8/2001 | Burcham et al. | |
| 7,005,068 | B2 * | 2/2006 | Hoffland | 210/603 |
| 7,452,465 | B2 * | 11/2008 | Le | 210/603 |
| 2004/0134853 | A1 | 7/2004 | Miller, III | |
| 2007/0251880 | A1 | 11/2007 | Herding et al. | |

FOREIGN PATENT DOCUMENTS

DE 3716637 A1 * 12/1988
KR 10-0703890 B1 4/2007

OTHER PUBLICATIONS

PCT International Search Report and Written Opinion, PCT Application No. PCT/US2009/058330, Apr. 27, 2010, 9 pages.
Todd, J. et al., "Ecological Design Applied," Ecological Engineering, 2003, pp. 421-440, vol. 20.

* cited by examiner

Primary Examiner—Fred Prince
(74) Attorney, Agent, or Firm—Fenwick & West LLP

(57) ABSTRACT

A lagoon of effluent is established, comprising a set of sub-portions at different levels in the lagoon associated with a corresponding set of concentrations of dissolved oxygen, each sub-portion of the lagoon having a different concentration of dissolved oxygen. An incubator comprising a set of sub-portions associated with said set of concentrations of dissolved oxygen is established, each sub-portion of the incubator having a different concentration of dissolved oxygen. A volume of effluent from each sub-portion of the lagoon is transmitted to a corresponding sub-portion of an incubator having a substantially similar concentration of dissolved oxygen as said sub-portion of the lagoon. A first remediated volume of effluent is generated in said corresponding sub-portion of the incubator responsive to proliferating a first microorganism which uses a first compound in said volume of effluent as substrate for growth, the first microorganism enabling a first chemical reaction which alters the first compound.

16 Claims, 6 Drawing Sheets

MICRO GAS ATTENDANT SYSTEM

BACKGROUND OF THE INVENTION

1. Field of the Invention

This invention pertains in general to a system for remediation of biological waste, and more particularly to a system for remediation of livestock waste through aerobic and anaerobic bacterial digestion.

2. Description of the Related Art

As the global population increases there is a corresponding need to increase food production. Large scale food production operations such as concentrated animal feeding operations (CAFOs) produce large volumes of livestock waste. Livestock waste can contain compounds such as manure, fertilizer compounds, hydrocarbons and antibiotics. Many of these compounds must be remediated in order to attenuate negative environmental impact caused by the compounds. Accordingly, efficient methods of livestock waste remediation are needed to support environmentally sustainable food production for a growing global population.

One popular method of livestock waste remediation is through the use of livestock waste lagoons. A livestock waste lagoon is a sealed tank into which liquid livestock waste is combined with water to create an effluent for remediation. Typically, the liquid livestock waste is combined with water collected from rainfall. Livestock waste lagoons act as "digesters" in which anaerobic or aerobic bacteria decompose the compounds in the effluent into gases, liquids and sludge, thus remediating the compounds. Anaerobic bacteria are bacteria which do not survive in the presence of free oxygen. Aerobic bacteria require free elemental (dissolved) oxygen for survival.

Anaerobic lagoons are most commonly used for livestock waste treatment. Anaerobic bacteria can decompose or "digest" more organic compounds per unit lagoon volume than aerobic bacteria and are predominantly used for treatment of concentrated organic waste. Since anaerobic digestion is not dependent on dissolved oxygen, lagoons can be much deeper and require less surface area, thus enabling a greater volume of waste to be remediated. However, anaerobic digestion results in the production and emission of noxious gases, primarily hydrogen sulfide, ammonia, and intermediate organic acids.

Aerobic lagoons remediate livestock waste through digestion of the waste by aerobic bacteria. The main advantage of aerobic lagoons is that aerobic digestion of livestock waste tends to more thoroughly remediate organic compounds present in effluent than anaerobic digestion. Aerobic digestion of livestock waste also produces relatively odor-free end products.

In aerobic lagoons, oxygen diffusion occurs across the surface of the lagoon resulting in an increased dissolved oxygen concentration which enables the proliferation of aerobic bacteria. Because of the need for an increased dissolved oxygen concentration, naturally aerobic lagoons are designed on the basis of surface area rather than volume. Water depths of aerobic lagoons are typically shallow, ranging from 3 to 5 feet. Consequently, large amounts of land are required for naturally aerobic lagoons—as much as 25 times more surface area and 10 times more volume than an anaerobic lagoon 10 feet deep. Thus, naturally aerobic lagoons are impractical and are generally not used for livestock waste remediation. To compensate for lack of surface area, some aerobic lagoons are mechanically aerated.

Double-stage lagoons provide one method of combining the benefits of aerobic digestion and anaerobic digestion of livestock waste. In double stage lagoons, incoming waste is first input to an anaerobic first-stage lagoon. Overflow from the anaerobic first-stage lagoon is output to an aerobic second-stage lagoon. This produces an effluent end product that has less odor and fewer organic solids than anaerobic digestion alone. However, double-stage lagoons require the maintenance of two separate lagoons and their respective bacterial populations. Further, the anaerobic first-stage lagoon still produces noxious gases.

Accordingly, there is a need for systems which maximize both the efficiency of remediation and completeness of remediation. There is an additional need for systems which utilize the by-products of remediation.

BRIEF SUMMARY

One embodiment of the present invention includes a method for remediating an effluent containing livestock waste. The micro gas attendant system establishes a lagoon of waste effluent. The lagoon comprises a set of sub-portions or "levels", each level having a unique concentration of dissolved oxygen according to an oxygen gradient present in the lagoon. The micro gas attendant system transmits the effluent from each level of the lagoon to a corresponding level of an incubator having a same concentration of dissolved oxygen as the level of the lagoon. The incubator contains a set of microorganisms which digest organic compounds in the effluent, generating a remediated effluent. The micro gas attendant transmits the effluent and micro-organisms from the incubator to the lagoon.

Another embodiment of the present invention includes method for proliferating algae using by-products of anaerobic digestion. The micro-gas attendant system transmits anaerobic waste from an anaerobic level of the lagoon to a reaction vessel containing meso-thermophilic and thermophilic bacteria. The meso-thermophilic and thermophilic bacteria perform anaerobic digestion of the anaerobic waste in the reaction vessel. The micro-gas attendant system collects gaseous by-products from anaerobic digestion in a manifold. The micro-gas attendant system transmits gaseous by-products from the manifold to growth tubes containing algae. The algae proliferate in the growth tubes, consuming the gaseous by-products. The micro-gas attendant system transmits algae from the growth tubes to a level of the lagoon where the algae contribute to the dissolved oxygen concentration of the level by performing photosynthetic reactions.

Another embodiment of the present invention includes a method for producing methane. As described above, the micro-gas attendant system collects gaseous by-products from anaerobic digestion in a manifold. The micro-gas attendant system transmits the gaseous by-products to a filter. The micro-gas attendant system filters the gaseous by-products to produce methane.

DETAILED DESCRIPTION OF THE INVENTION

Figure 1:
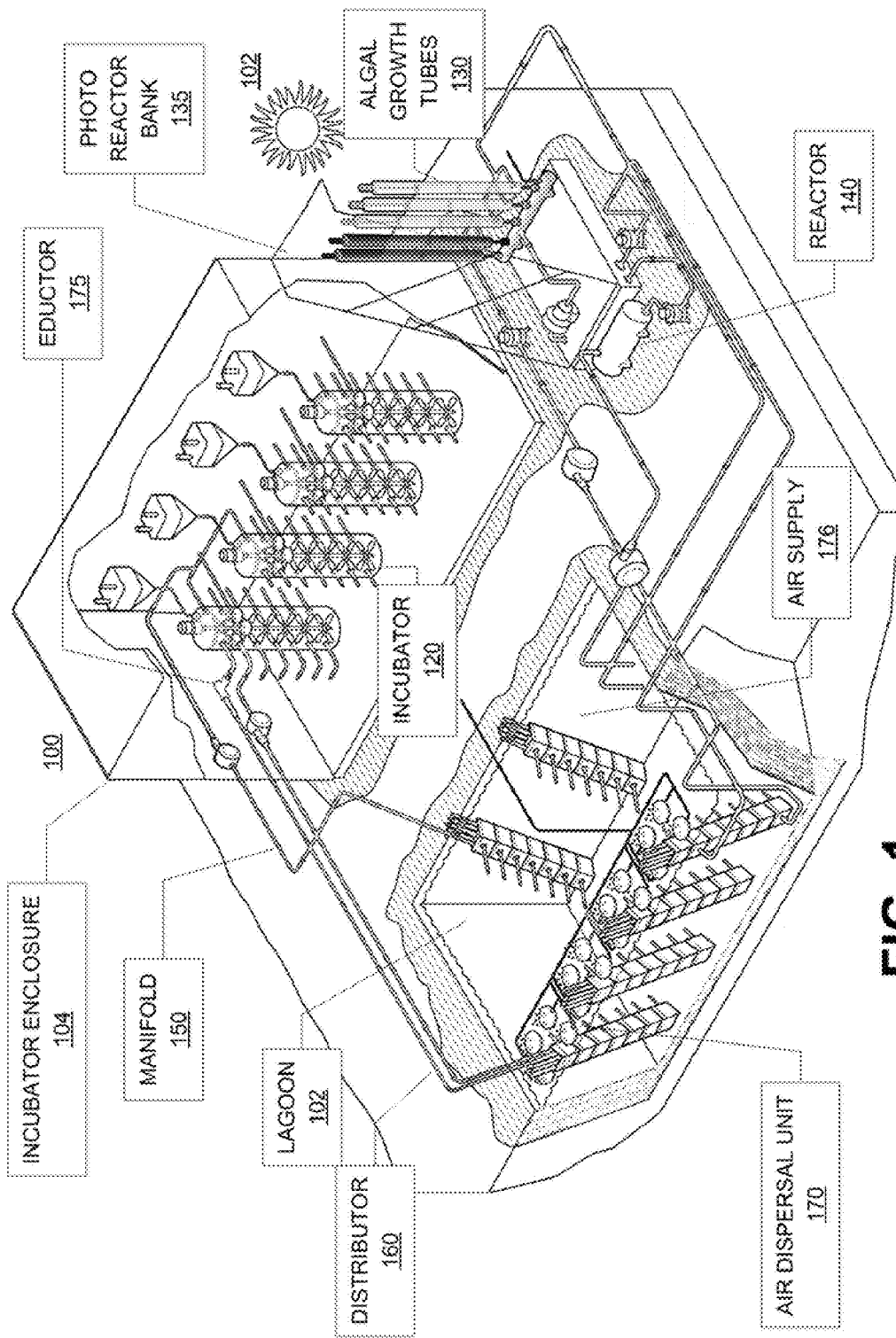
FIG. 1 is a high-level diagram of the micro gas attendant system according to one embodiment.

FIG. 1 is a high-level diagram of the micro gas attendant system 100. The micro gas attendant system 100 functions to remediate livestock waste produced by large scale livestock production operations such as concentrated animal feeding operations (CAFOs). Remediation, as used herein, refers to a process by which matter is processed to remove compounds from the matter and/or transform the compounds in the matter (e.g. chemically transform the compounds into other compounds) such that negative environmental impact of the matter is attenuated in the resultant matter. Livestock waste can include but is not limited to manure, environmental pathogens, organic compounds and inorganic compounds. The specific composition of livestock waste can be based on factors including: the feed used by the livestock production operation, the fertilizer used by the livestock production operation, antibiotics used by the livestock production operation, organic compounds such as hormones used by the livestock production operation and other compounds present in the livestock production operation such as hydrocarbons and sulfur containing compounds.

The micro gas attendant system 100 remediates livestock waste through the proliferation of microorganisms and macroorganisms which remediate or "digest" compounds in livestock waste through chemical reactions in which the compounds are used as substrate to proliferate the bacteria. The proliferating bacteria facilitate or perform chemical reactions which remediate the compounds. Microorganisms, as referred to herein, include eukaryotic microorganisms, prokaryotic microorganisms and photosynthetic eukaryotic microorganisms. Macroorganisms which remediate organic compounds can include members of the algae family.

The micro gas attendant system 100 comprises a lagoon 102. A lagoon 102, as referred to herein, is a three dimensional receptacle used to hold a volume of effluent. Effluent, as described herein, is composition of liquid livestock waste and water. Depending on the stage in remediation, the organic compounds in the effluent may be partially remediated or fully remediated. In one embodiment, the lagoon is 946 feet long, 71 feet wide and 18 feet deep with a storage capacity of 551,000 ft$^3$.

The lagoon 102 is divided into pressure sensitive horizontal sub-portions or "levels" according to an oxygen gradient. In one embodiment, each level has a pressure of 0.4 pounds per square inch (psia). In the embodiment illustrated, the lagoon 102 is horizontally divided into seven horizontal levels. The surface level and the level immediately below the surface level (level 1 and level 2, respectively) contain the highest concentrations of dissolved oxygen and are collectively referred to as the "aerobic levels". The level at the bottom of the lagoon (level 7), contains no dissolved oxygen and is referred to as the "anaerobic level". The levels between the aerobic levels (levels 1 and 2) and anaerobic level (level 7) and are collectively referred to as the facultative levels (levels 3, 4, 5 and 6). These levels have respective concentrations of dissolved oxygen which are inversely proportional to their distance from the surface of the lagoon 102. In a specific embodiment, one or more of the aerobic levels have a maximum regulated oxygen concentration of 5 mg/L.

The effluent at each respective level of the lagoon 102 comprises a concentration of oxygen, composition of compounds, and composition of organisms that is unique to the level. The different oxygen concentrations at each of the levels result in the proliferation of microorganisms and macroorganisms that are specific to the oxygen concentrations. The composition of microorganisms and macroorganisms at each level alters the composition of the effluent at the level through "digestion" of compounds in the effluent. Consequently, the types of compounds that are remediated at each level are different based on the types of organisms that proliferate at the oxygen concentration of the level. This difference in remediation due to difference in oxygen concentration at each level is referred to as "stratification". As stratification allows for different types of compounds to be remediated, the remediation of the effluent is more thorough or "complete" than in systems which perform remediation at a homogenous oxygen concentration.

The micro gas attendant system 100 receives un-remediated effluent, referred to herein as "influent" from livestock operations. In a specific embodiment the water is received from a flush system. The amount of influent received by the micro gas attendant system 100 may vary based on the number of animals in the livestock operation. The amount of water received per animal per day can range from 40-70 gallons and the amount of solid waste received per animal per day can range from 80-150 pounds depending on the weight of the animal.

The micro gas attendant system 100 remediates the influent to produce liquid effluent which has essentially had all compounds with negative environmental impact removed. The micro gas attendant system 100 further remediates the influent to output liquid effluent which essentially has had all compounds with negative environmental impact removed, and solid biomass. The liquid effluent output from the micro-gas attendant system 100 is used in agricultural processes such as irrigation. The solid biomass output from the micro-gas attendant system 100 is used as non-toxic bedding in dairy operations and as fertilizer in agricultural processes.

The influent and effluent is assessed to determine the amount of undesirable compounds before, after and during remediation. Suitable methods of assessing the amount of undesirable compounds in the influent and effluent are outlined in the 21$^{st}$ Edition of "Standard Methods for the Examination of Water and Wastewater" published by the American Public Health Association (APHA), the American Water Works Association (AWWA) and the Water Environment Federation (WEF). If the amount of undesirable compounds in the effluent indicates that the effluent is effectively remediated, the micro-gas attendant system 100 outputs the liquid effluent.

The micro gas attendant system 100 comprises an incubator enclosure 104 containing one or more incubators 120. The micro gas attendant system 100 uses the incubators 120 to proliferate specific types of bacteria using effluent from the lagoon. In the incubators 120, compounds in the effluent are further "digested" by the proliferating bacteria. According to the embodiment, different incubators 120 may be used to proliferate different groups of bacteria, different species of bacteria or different strains of bacteria. In one embodiment, the different incubators 120 are used to proliferate different groups of bacteria, where the groups of bacteria are based on the types of compounds they digest. The proliferation of each group of bacteria is dependent upon the concentration of the type of compounds they digest. Therefore, a high concentration of a compound in the effluent will cause corresponding proliferation of the type of bacteria which digests the compound.

In a specific embodiment the different incubators 120 are used to proliferate phosphobacteria, nitrobacteria, sulfbacteria and hydrocarbon-degrading bacteria. Phosphobacteria, as used herein, refers to bacteria which possess the ability to solubilize insoluble inorganic phosphate, making it bio-available to plants as fertilizer. The solubilization of inorganic phosphate is due to the production of organic acids by these organisms. Phosphobacteria are also known to produce amino acids, vitamins and growth promoting substances like indole acetic acid (IAA) and gibberellic acid (GA3) which help to improve growth of plants.

Sulfbacteria, as used herein, refers to sulfur-reducing bacteria and sulfate-reducing bacteria. Sulfur-reducing bacteria comprise several groups of bacteria that reduce elemental sulfur to hydrogen sulfide. They couple this reaction with the oxidation of acetate, succinate or other organic compounds. Sulfate-reducing bacteria use sulfate as an oxidizing agent, reducing it to sulfide. Most sulfate-reducing bacteria can also digest other oxidized sulfur compounds such as sulfite and thiosulfate, or elemental sulfur. This type of chemical reaction is called dissimilatory, since sulfur is not incorporated—assimilated—into any organic compounds. Sulfate-reducing bacteria are common in anaerobic environments.

Nitrobacteria, as used herein, refers to bacteria that oxidize ammonium compounds into nitrites and/or nitrites into nitrates. Nitrobacteria are commonly found in aerobic environments such as soil. Hydrocarbon-degrading bacteria, as used herein, refers to bacteria which have the ability to catalyze the degradation of hydrocarbons such as oil found in the environment.

Like the lagoon 102, each incubator 120 is divided into levels where each level has a different oxygen concentration according to the level. In most embodiments, the number of levels in the lagoon 102 and the number of levels in the incubator 120 correspond.

The distributor 150 and manifold 160 each comprise a set of pipes which connect the levels in the lagoon to corresponding levels in the incubator. Each incubator 120 receives effluent from the lagoon 102 via a manifold 160. Each incubator 120 transmits effluent back to the lagoon 102 via a distributor 150. In the embodiment illustrated in FIG. 1, the distributor 150 and manifold 160 comprises 7 pipes which connect 7 levels of the lagoon 102 to 7 corresponding levels in the incubator 120. In some embodiments, the distributor 150 further contains an extra pipe used to disturb or push out settlement at the bottom of the lagoon during installation.

In a specific embodiment, the distributor 150 and/or manifold 160 are constructed using 3 inch diameter stainless steel pipe casing with 7 distribution chambers (one for each level). The casing is attached to a 6 inch steel beam rail at the top only and guided at the bottom. This casing could be removed for maintenance purposes and re-installed easily without removing support rail. A small concrete pad at grade level anchors the rail. A shut-off and disconnect valve as well as an air bypass valve may be provided for each of the pipes. In case of build up or plug up situations, the individual pipe can be blown out with compressed air.

The distributor 150 and manifold 160 also may have different rates of flow. In one embodiment, the pipes in the distributor 150 have a flow rate of 0.5 to 1 gallons per minute (gpm) and the pipes in the manifold 160 have a flow rate twice as much as the distributors (i.e. 1 to 2 gpm).

In some embodiments, the distributors 150 contain air dispersal systems 170. In these embodiments, an eductor 175 is used to educt air for continuation of bacteria growth in the pipe connecting level 1 of the lagoon to level 1 of the incubator. In the embodiment illustrated, there are air dispersal units 170 suspended below level 2 on each of the distributors 150. In a specific embodiment, each air dispersal unit 170 comprises a 4 inch diameter pipe header equipped with fine bubble membrane air diffusers that are 20 inches in diameter and provide approximately 5 standard cubic feet per minute (scfm) of oxygen. In some embodiments, the air dispersal unit 170 can also disassemble from the top for maintenance. In the embodiment illustrated, the diffusers are arranged in a semi-circle. In a specific embodiment, the diffusers are arranged in a semi-circle that is 3 feet in diameter. In the embodiment illustrated, each of the air dispersal units 170 is connected to a single air supply 176.

The micro gas attendant system 100 further comprises a photo reactor bank 135 that includes a reactor 140 and a set of algal growth tubes 130. The reactor 140 proliferates thermophilic and/or mesophilic bacteria that "digest" waste through anaerobic reactions which remediate organic compounds in the waste. The reactor 140 collects greenhouse gases (e.g. $CO_2$, methane and nitrous oxide) released from thermophilic and mesophilic bacterial digestion of solid waste and transmits the greenhouse gases to the algal growth tubes 130. The algae growth tubes 130 proliferate algae that consume greenhouse gases. The reactor 140 and algal growth tubes 130 as described in detail below with respect to FIG. 4

Figure 2:
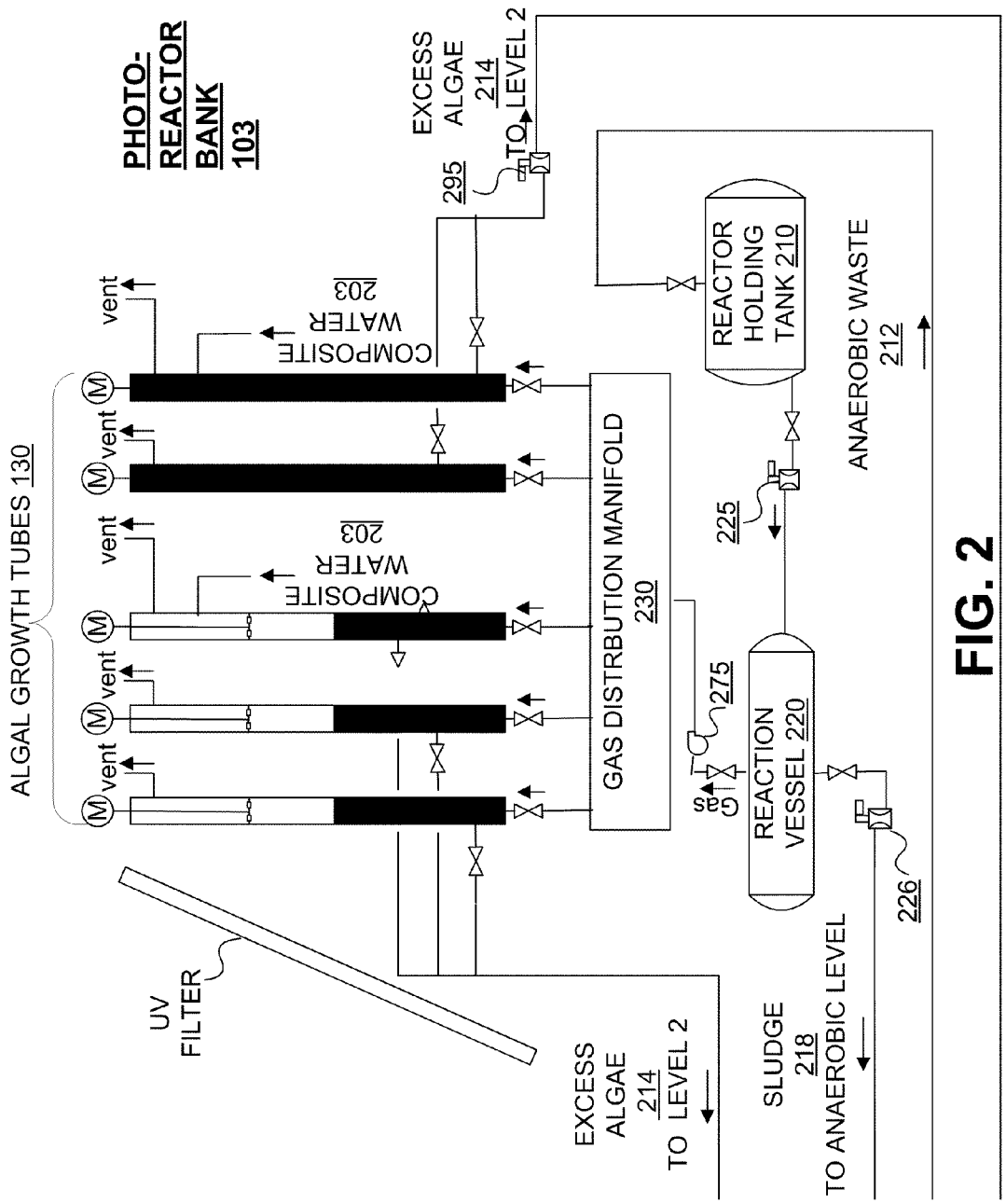
FIG. 2 is a detailed diagram illustrating the photo-reactor bank according to one embodiment.

FIG. 2 illustrates the photo reactor bank 135 that comprises a reactor 140 and a set of algal growth tubes 130. The reactor 140 performs anaerobic digestion of waste. The anaerobic digestion process begins with bacterial hydrolysis of the input materials in order to break down insoluble organic polymers such as carbohydrates and make them available for other bacteria. Acidogenic bacteria then convert the sugars and amino acids into carbon dioxide, hydrogen, ammonia, and organic acids. Acetogenic bacteria then convert these resulting organic acids into acetic acid, along with additional ammonia, hydrogen, and carbon dioxide. Methanogenic bacteria convert these products to methane and carbon dioxide. Suitable Acidogenic, Acetogenic and Methanogenic bacteria for proliferation in the reactor 140 are listed in Appendix A. Acidogenic, Acetogenic and Methanogenic bacteria that are commercially available from the America Type Culture Collection (ATCC) Biological Resource Center of Manassas, Va. are listed in Appendix A in association with their ATCC Catalog Numbers.

According to the embodiment, the Acetogenic, Methanogenic and Acidogenic bacteria may either be thermophilic bacteria, mesophilic bacteria or any combination thereof. Thermophilic bacteria, as referred to herein, are bacteria which thrive at high temperatures (between 45 and 80 degrees Celsuis). Mesophilic bacteria, as referred to herein, are bacteria which thrive at moderately high temperatures (between 15 to 40 degrees Celsuis). According to the embodiment, the reactor 140 may proliferate the thermophilic and/or mesophilic bacteria separately in different reactors 140 or in a same reactor 140 with a temperature gradient.

The reactor 140 receives anaerobic waste from an anaerobic level of the lagoon 102. In the illustrated embodiment, the reactor 140 receives anaerobic waste from level 7 of the lagoon. In one embodiment, the anaerobic waste received is an effluent containing 20% to 30% suspended solid matter. In some embodiments, the reactor 140 comprises a holding tank 210 used to store anaerobic waste prior to digestion. In a specific embodiment, the holding tank 210 has a capacity of 100 gallons (400 liters). In some embodiments, the holding tank 210 comprises an agitator used to keep the solid matter suspended in the effluent.

The reactor 140 further comprises a reaction vessel 220 in which the thermophilic and/or mesophilic bacteria perform anaerobic digestion of waste. The reaction vessel 220 receives anaerobic waste from the holding tank. The rate at which the reaction vessel 220 receives anaerobic waste from the holding tank is based on the rate at which greenhouse gases are produced by anaerobic digestion of the waste in the reaction vessel 220. In the embodiment illustrated, the reaction vessel 220 receives anaerobic waste from the holding tank 210 using a pump 225. In a specific embodiment, the reaction vessel 220 receives anaerobic waste from the holding tank 210 by gravity flow.

The reaction vessel 220 is heated to optimize proliferation of thermophilic and/or mesophilic bacteria for anaerobic digestion. According to the embodiment, the temperature may range from 97 to 145 degrees Fahrenheit. In a specific embodiment the temperature is 99 degrees Fahrenheit. In one embodiment, the reaction vessel 220 is an enclosed sloped vessel with heated bottom. In this embodiment, a thermal blanket (e.g. a steam blanket or hot water blanket) provides heat to the bottom of the reaction vessel 220. A pump 226 is located at the bottom of the slope to collect solid products of anaerobic digestion 218, herein referred to as "sludge", and pump the sludge 218 to the anaerobic level of the lagoon. In most embodiments, the reaction vessel 220 is an air tight steel vessel with controls to regulate pressure, temperature and level, and controls to analyze gas produced in the reaction vessel 220. According to the embodiment, the size of the reaction vessel 220 may vary depending on the time and surface area necessary for anaerobic digestion.

The reaction vessel 220 is connected to a gas distribution manifold 230 which transmits gaseous by-products of anaerobic digestion from the reaction vessel 220 to the algal growth tubes 130. The gas distribution manifold 230 stores gas collected in the reaction vessel 220 by an explosion-proof air blower 275. In most embodiments, the gas distribution manifold 230 is under slight positive pressure (e.g. 12 psi) to overcome the water column in the algae growth tubes 130. The gas distribution manifold 230 comprises flow control valves used to regulate the amount of gas flow to each algal growth tube 130 for proper algae growth. The gas distribution manifold 230 further contains safety features such as a pressure relief valve and an explosion rupture disc.

In alternate embodiments, the gas distribution manifold 230 transmits greenhouse gas from the reaction vessel 220 to a methane refinery. The methane refinery comprises an activated charcoal filter which is used to remove hydrogen sulfide from the gaseous by-product. The methane refinery further comprises a reaction chamber in which the gaseous by-product is pressurized to approximately 600 pounds per square inch and passed through water to remove carbon dioxide and carbonic acid. Once hydrogen sulfide, carbon dioxide and carbonic acid are removed, the gaseous by-product is primarily comprised of methane.

The algal growth tubes 230 are cylindrical containers used to proliferate algae. Algae, as used herein, can refer to any type of algae including both prokaryotic algae (blue-green bactera) and eukaryotic algae. Suitable algae for proliferation in the algal growth tubes 230 are listed in Appendix A. Algae that are commercially available from the ATCC and Carolina Biological Supply Company of Burlington, N.C. are listed in Appendix G in association with their Catalog Numbers.

According to the embodiment, the algal growth tubes 130 may be clear in order to provide the algae with light for photosynthesis and/or the algal growth tubes 130 may be black in order to force the algae to use pathways for energy metabolism other than photosynthesis. In most embodiments, the set of algal growth tubes 130 comprises clear algal growth tubes and radiation opaque or "black" algal growth tubes. In a specific embodiment, the set of algal growth tubes 130 comprises 3 clear algal growth tubes and 2 black algal growth tubes. The algal growth tubes 130 are typically made from plastic such as acrylic or polyurethane. According to the embodiment the algal growth tubes can range from 5 to 17 feet high. In a specific embodiment, the algal growth tubes are 10 feet high.

Initially, the algal growth tubes 130 are filled with composite water 203 from an aerobic level of the lagoon 120 and stock algae in order to seed algae proliferation. In most embodiments, the algal growth tubes 130 are refilled with fresh composite water 203 from an aerobic level of the lagoon 102 daily. The algal growth tubes 130 receive gas from the gas distribution manifold 230. The rate at which the algal growth tubes 130 receive gas from the gas distribution manifold 230 is dependent upon the consumption of the gas by the algae. In some embodiments, the algal growth tubes 130 contain a check valve used to ensure water does not enter the gas manifold.

The algal growth tubes 130 are heated to optimize proliferation of algae. In a specific embodiment, each algal growth tube 130 is heated to maintain a temperature of about 77 degrees Fahrenheit. The clear algal growth tubes 130 are provided with sunlight or artificial light in order to enhance algae proliferation and greenhouse gas consumption. In most embodiments, the clear algal growth tubes 130 receive a minimum of 10 hours of sunlight per day. In a specific embodiment, the clear algal growth tubes 130 are provided with artificial light using high pressure sodium lights (e.g. 50 watts per sq ft for an approximate sunlight equivalent). In some embodiments, a supplemental ultra violet light bank 205 is used to provide artificial light to the algal growth tubes 130.

Excess algal growth 214 in the algal growth tubes 130 is reduced by a specified amount on a periodic basis in order to allow for continued proliferation of algae. The excess volume of algae 214 from the reduction is then pumped back to the lagoon 120. In a specific embodiment, the volume of algae in the algal growth tubes 130 is reduced by 50% every 24 hours. In some embodiments, the excess volume of algae 214 may be reduced in order to maintain constant temperatures in the algal growth tubes 130 (e.g. in order to maintain a temperature of 77 degrees Fahrenheit in the algal growth tubes). In one embodiment, the algal growth tubes 130 contain a high speed chopper used to chop agglomerated excess volume of algae 214 into to a manageable size in order to facilitate reduction. In a specific embodiment, the excess volume of algae 214 is pumped to an aerobic level of the lagoon using a diaphragm pump 295.

Figure 3:
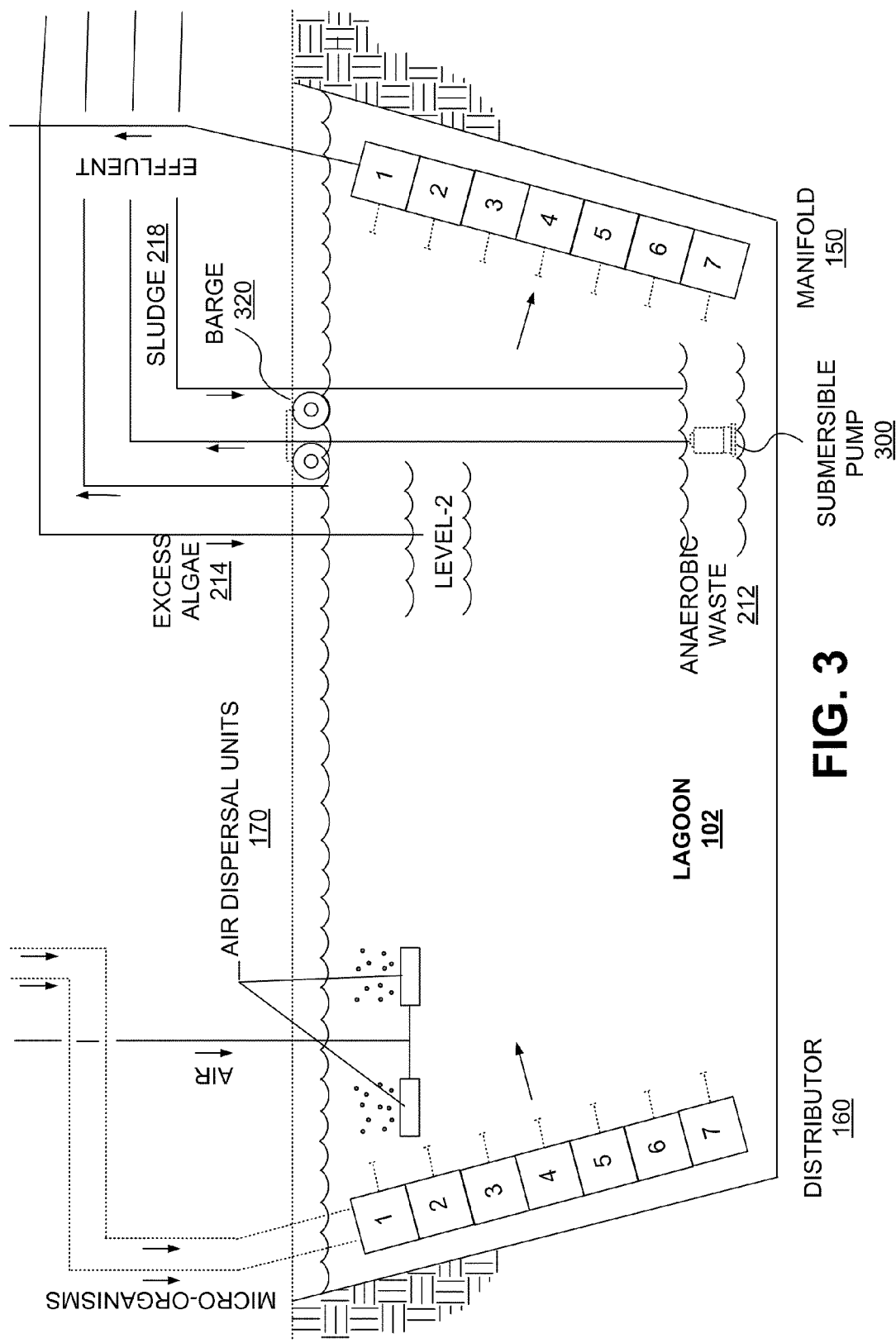
FIG. 3 is a detailed diagram illustrating the lagoon according to one embodiment.

FIG. 3 is a detailed diagram illustrating the lagoon 102 according to one environment. As discussed above, the distributor 160 functions to transmit micro-organisms and effluent from the incubators 120 to the lagoon 102. The manifold 150 functions to transmit effluent from the lagoon 102 to the incubators 120. Excess algae 214 are transmitted from the algal growth tubes 130 to an aerobic level of the lagoon 102. In the illustrated embodiment, the lagoon 102 comprises 7 levels, and the Micro-gas Attendant System 100 transmits excess algae 214 to the level directly beneath the surface level of the lagoon 102 (level 2). The Micro-gas Attendant System 100 transmits sludge 218 is transmit to the anaerobic level (level 7) of the lagoon 102.

The Micro-gas Attendant System 100 transmits anaerobic waste from the anaerobic level of the lagoon 102 to the reactor 140. In the embodiment illustrated, a submersible pump 300 is used to pump the anaerobic waste from the lagoon 102 to the reactor 140. In a specific embodiment, the submersible pump 300 is a submersible grinder pump with a capacity of 45 gallons per minute (gpm). The submersible pump 300 is suspended under a monorail under a movable barge 320 spanning across the lagoon. The submersible pump 300 is moved at a slow speed of approximately 1 foot per minute across the lagoon by a cable system. The barge 320 moves along the rails of a truss structure spanning across the lagoon 102, and is mounted on wheels on both ends. The barge 320 can be repositioned up and down the lagoon between the end distributors remotely using a GPS device.

Figure 4:
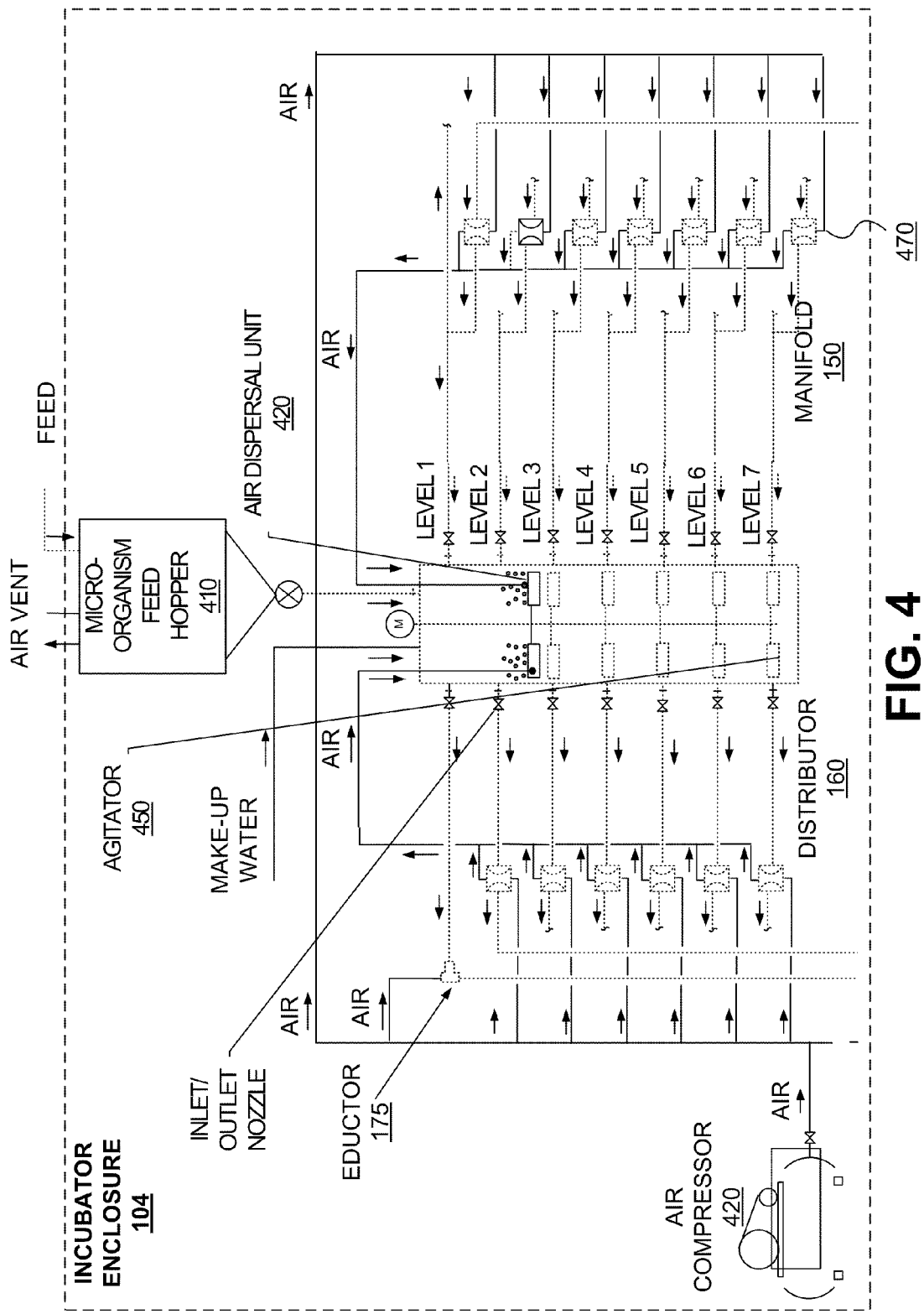
FIG. 4 is a detailed diagram illustrating the incubator enclosure according to one embodiment.

FIG. 4 is a detailed diagram illustrating the incubator enclosure 104 according to one embodiment. In FIG. 4, the incubator enclosure is illustrated with one incubator 120 for ease of description. In most embodiments, the incubator enclosure comprises a plurality of incubators 120.

The incubator enclosure 104 is a temperature-controlled, insulated enclosure comprising one or more incubators 120. In one embodiment, the incubator enclosure 104 is constructed with steel columns, beams, and insulated sandwiched panels. The incubator enclosure 104 houses the incubators 120, piping, pumps, micro-organism feed hoppers 140, and control instruments associated with the incubators 120. In one embodiment, a 2-ton HVAC unit is designed to maintain a temperature of 77° F. and provide appropriate ventilation for the incubator enclosure 104. In some embodiments, a water source heat pump and geothermal system is used to extract heat from underground to provide heating or air conditioning for the incubator enclosure 104. According to the embodiment, a separate enclosure may be used to host equipment that does not require insulation, heating, and air conditioning such as a compressor unit 420.

In most embodiments, a plurality of incubators 120 will be used to proliferate different types, species or strains of micro-organisms. These "wide spectrum" micro-organisms are stored in micro-organism feed hoppers 410 and feed into the incubators 120 using continuous feeders. Suitable Sulfbactera, Nitrobacteria, Phosphobacteria, Hydrocarbon-reducing bacteria and other bacteria for proliferation in the incubators 120 are listed in Appendix B, Appendix C, Appendix D, Appendix E and Appendix F, respectively. Bacteria that are commercially available from the America Type Culture Collection (ATCC) Biological Resource Center are listed in the appendices in association with their ATCC Catalog Numbers. In addition to the specific types, species or strains of micro-organism fed into the incubator for proliferation, other micro-organisms already present in the effluent may be proliferated in the lagoon 102 and/or the incubators 104.

According to the embodiment, the micro-organisms fed into the incubators 120 from the micro-organism feed hoppers 410 may be liquid micro-organisms, dry solid micro-organisms or any combination thereof. In most embodiments, the micro-organism feed hopper 410 is filled with liquid micro-organisms and/or dry solid micro-organisms through a nozzle from the rooftop of the incubator enclosure 104.

Each incubator 120 is fed microorganisms through a feeding system. According to the embodiment, the micro-organisms may be fed into the incubator 120 through a wet feeding system or a dry feeding system. The wet feeding system and the dry feeding system feed the incubators 120 at a flow rate defined to maintain a specified concentration of micro-organisms in the incubators 120 (e.g. 50 parts per million).

In one embodiment, the dry feeding system is an adjustable loss-in-weight feeding system with a constant flow rate, similar to the one uses in pharmaceutical practices. In a specific embodiment, the dry feeding system is used with a micro-organism feed hopper 410 with a capacity of 5 cu ft of dry solid micro-organisms. The flow rate at which dry solid micro-organisms are fed into the incubators using the dry feeding system is 0.25 cu ft per day.

In one embodiment, the wet feeding system is a tube and valve system which uses the force of gravity to discharge liquid micro-organisms to the incubators 120 at a defined flow rate. In a specific embodiment, the wet feeding system is used with a micro-organism feed hopper 410 with a capacity of approximately 35-gallons of liquid micro-organisms. The flow rate at which liquid micro-organisms are fed into the incubators 120 using the wet feeding system is 1.8 gallon per day.

The incubators 120 are controlled to a constant temperature (e.g. 77° F.), balanced pH, and equipped with an air dispersal device. In some embodiments, heating blankets are required to maintain the incubators at a constant temperature. The incubators are connected to a freshwater makeup system designed to supplement the effluent with fresh water in order to maintain the incubator levels to a constant level.

The height of the incubators 120 is equivalent to the depth of the lagoon 102 in order to maintain same pressure differential the corresponding levels of the lagoon 102 and the incubators 120. The level of effluent in the incubators 120 is maintained at the same height as the level of effluent in the lagoon in order to eliminate differential pressure that could slow the proliferation of micro-organisms. In one embodiment, the incubators 120 are 1 to 6 feet in diameter and 16 feet high. According to the embodiment, the incubators 120 may be constructed from stainless steel, fiberglass, plastic or any combination thereof.

The incubators contain air dispersal units 420. The air dispersal units 420 contain a plurality (e.g. 4) of fine bubble membrane air diffusers. In a specific embodiment, each diffuser is 9 inches in diameter and provides a flow rate of approximately 10 standard cubic feet/minute (scfm) of oxygen. In the embodiment illustrated, each air dispersal unit 420 is positioned at the bottom of the second level of the incubator 140. The air dispersal units receive air from the diaphragm pumps in the manifold 150 and distributor 160.

At each level, the incubators 120 are equipped with agitators 450 which agitate effluent within each level in order to facilitate proliferation of microorganisms. The agitators 450 include a set of paddles designed to agitate effluent in the incubators 120 while limiting up or downward transfer. The agitators 450 run at a low speed of 1 rotation per minute (rpm). According to the level of the incubator, the agitators 450 may have different numbers of paddles for increased agitation. In a specific embodiment, the agitator 450 at the anaerobic level (i.e. level 7) has 2 paddles; the agitator 450 at level 6 has 6 paddles and the agitators 450 at the facultative levels have 18 paddles. According to the embodiment, the width of paddles may vary according to the levels with increased width providing increased proliferation within the levels.

As discussed above, each incubator 120 receives effluent from the lagoon 102 at a pre-determined flow rate through a manifold 150 comprising a set of inlet pipes which connect corresponding levels of the lagoon 102 with corresponding levels of the incubator 120. Effluent is transmitted from the incubator 120 to the lagoon 102 at a pre-determined flow rate through a distributor 160 comprising a set of outlet pipes which connect corresponding levels of the incubator with corresponding levels of the lagoon 102. The manifold 150 and the distributor 160 further comprise pumps 470 used to extract effluent from the levels of the lagoon 102 and pump the effluent containing microorganisms proliferated in the incubators back to the corresponding levels in the lagoon 102.

In the embodiment, illustrated the manifold and distributor comprise diaphragm pumps 470.

The pumps 470 are powered by a compressor unit 420 providing medium pressure (40-60 psi) for the operation of the pumps 470. In most embodiments, the compressor unit 420 is located outside the incubator enclosure 102 and in a separate enclosure without temperature control. In one embodiment, the pumping system is powered by air using an air compressor 420. In a specific embodiment, the air compressor 420 is a rotary screw compressor comprising wet and dry air receivers, a heatless regenerative air dryer, particulate and coalescing filters, and flow control valves. The air dryer is required to desiccate air used for the operation of the diaphragm pumps 470. In some embodiments, the air dryer also controls the outlet air temperature by, for example, maintaining an outlet air temperature of 77° F. In the embodiment illustrated, exhaust from the diaphragm pumps 470 is transmit to the air dispersal units 420 in the incubator 140. A low pressure (e.g. less than 10 psi) regenerative blower supplies low pressure forced air for air dispersal unit 530 at the lagoon distributors. In this embodiment, intermediate compressed air is also used for blowing out the distributor 160 and/or the manifold 150. In some embodiments, coalescing filters are used to eliminate oil and dust from the compressor unit 420 in order to ensure clean air for microorganism proliferation.

The number of inlet pumps 470 in the manifold 150 and the number of outlet pumps 470 in the distributor 160 may vary according to the embodiment. In one embodiment, there are 14 inlet pumps 470 in the manifold 150 and 28 outlet pumps 470 in the distributor 150. In most embodiments, the inlet pumps 470 in the manifold 150 have a negative head of approximately 20 feet of water column and handle a flow rate of 1 to 2 gallons per minute. In most embodiments, the outlet pumps 470 in the distributor 160 do not have a static head but are used primarily for flow control, each outlet pump 470 having a flow rate of approximately 0.5 to 1 gallon per minute. The inlet and outlet pumps 470 are arranged in groups, labeled, and mounted against end walls of the incubator enclosure 104 and at an elevation accessible for maintenance.

A set of inlet and outlet nozzles connect the incubators 140 with the inlet pipes in the manifold 150 and outlet pipes in the distributor 160. The inlet and outlet nozzles are equipped with shutoff valves, temperature monitors and pH monitors. In one embodiment, the inlet and outlet pipes of each level are bundled together to maintain even temperature. In a specific embodiment, the inlet and outlet pipes are high-density polypropylene pipes. The piping systems are arranged so that the piping to and from two incubators is located at one end of the enclosure and the other two on the opposite end. The piping is arranged in two cable trays (cover and insulation optional) from the incubator enclosure to the lagoon. The outlet pipes are bundled together and float on the top level across the lagoon (i.e. between the ends). The floating pipes are anchored at the bank and the floatation provides a gradual heat transfer between lagoon temperature and incubator temperature to avoid growth shock.

The distributor 160 comprises steel pipes and tubing used for air distribution. In one embodiment, there are 2 air inlet and discharge collection headers for each pump 470 and 4 distribution air lines to the incubators 120. Temperature, pH, and flow instruments and controls are located at the inlet and outlet of incubators 120. The outlet piping of level one of the distributor 160 has an eductor 175 to add air to sustain growth during transfer.

Figure 5:
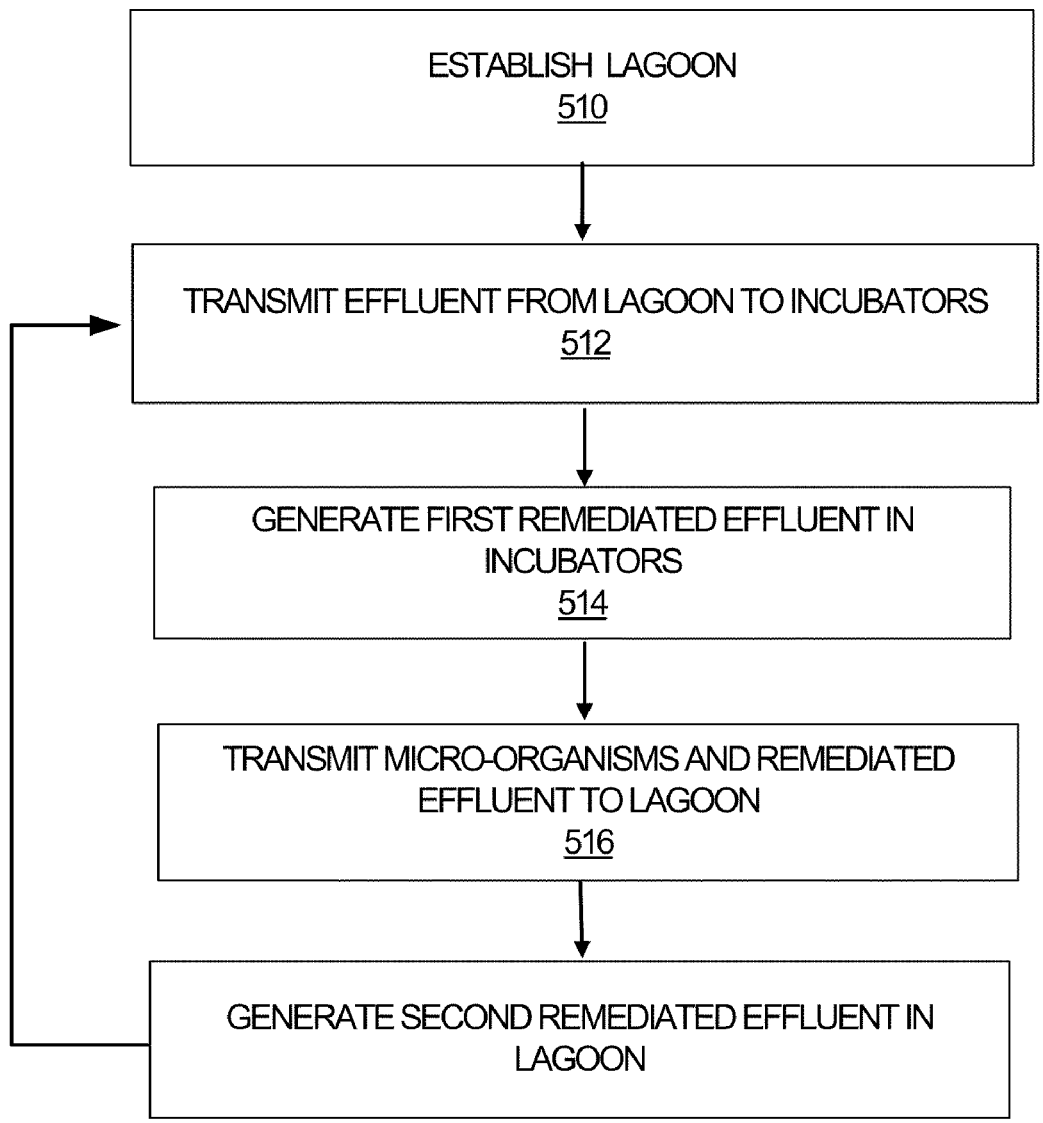
FIG. 5 is a flowchart illustrating steps performed by the micro gas attendant to remediate effluent according to one embodiment of the present invention.

FIG. 5 is a flowchart illustrating steps performed by the Micro Gas Attendant System 100 to remediate biological waste. Other embodiments may perform the illustrated steps in different orders, and/or perform different or additional steps.

The Micro Gas Attendant System 100 establishes 510 a lagoon containing effluent and transmits 512 the effluent from the lagoon 102 to the incubators 140. The Micro Gas Attendant System 100 generates 514 a remediated effluent responsive to proliferating micro-organisms in the incubators 140 which use compounds in the effluent as a substrate for growth, thus enabling a chemical reaction that transforms the organic compound. The Micro Gas Attendant System 100 transmits 516 the effluent and microorganisms from the incubators 140 to the lagoon 102. The Micro Gas Attendant System 100 generates 514 a remediated effluent in the lagoon 102 responsive to proliferating micro-organisms in the lagoon 102 which use compounds in the effluent as substrate for chemical reactions. The process is repeated until all of the compounds in the effluent are remediated.

Figure 6:
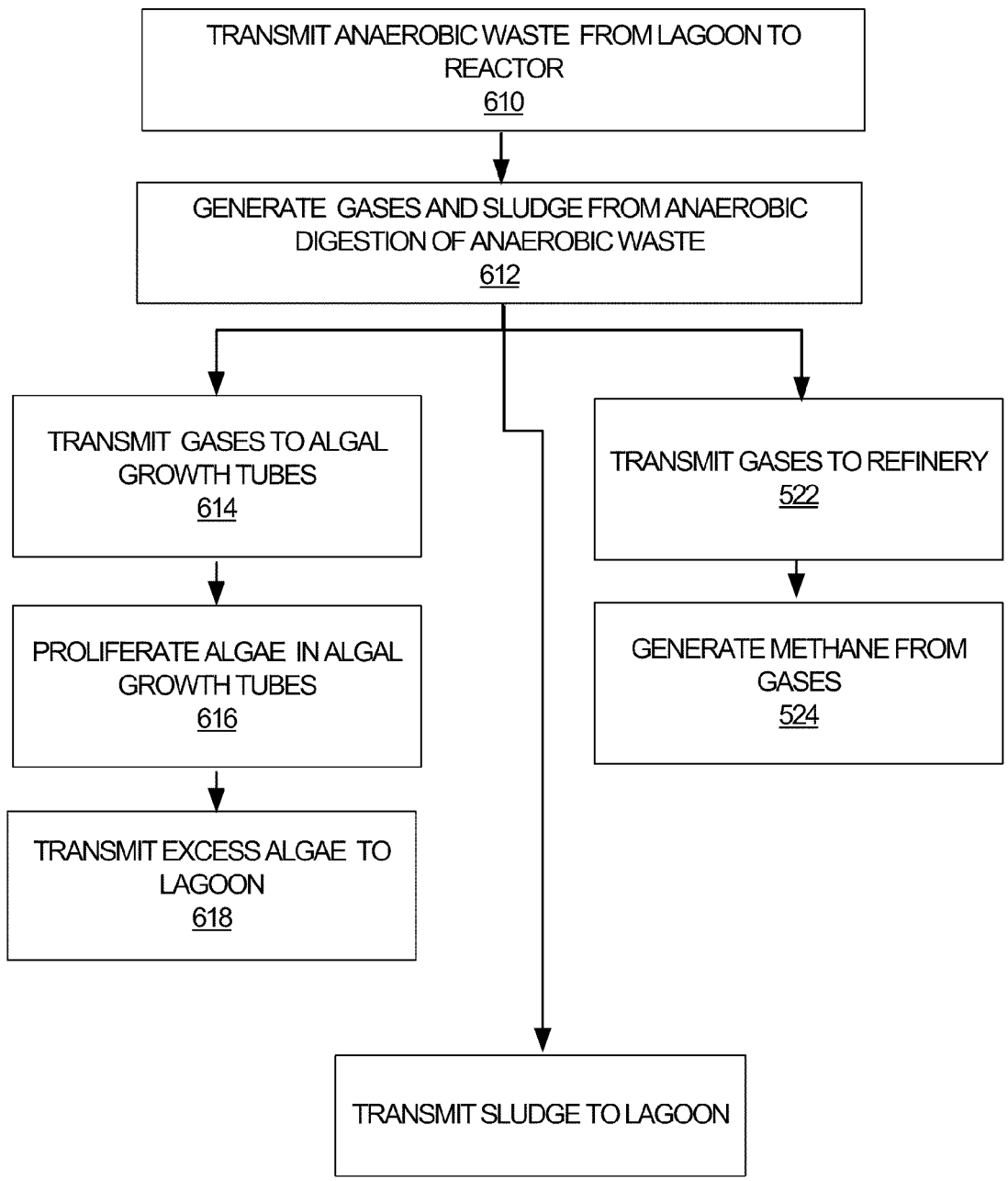
FIG. 6 is a flowchart illustrating steps performed by the micro gas attendant to proliferate algae and/or generate methane according to one embodiment of the present invention.

FIG. 6 is a flowchart illustrating steps performed by the Micro Gas Attendant System 100 to proliferate algae and generate methane. Other embodiments may perform the illustrated steps in different orders, and/or perform different or additional steps.

The Micro Gas Attendant System 100 transmits 610 anaerobic waste 212 from the lagoon 102 to a reactor 140. The Micro Gas Attendant System 100 generates 612 gas and sludge 218 responsive to proliferating anaerobic bacteria which digest the anaerobic waste 212. The Micro Gas Attendant System 100 transmits 614 the gas to algal growth tubes 130 and/or transmits the gas to a refinery. The Micro Gas Attendant System 100 proliferates 616 algae which consume the gas and produce oxygen in the algal growth tubes 130. The Micro Gas Attendant System 100 transmits 618 excess algae from the algal growth tubes 130 to the lagoon 102 and also transmits 522 gases to a refinery. The Micro Gas Attendant System 100 generates 524 methane by removing hydrogen sulfide, carbon dioxide and carbonic acid from the transmitted gases. The Micro Gas Attendant System 100 transmits sludge 218 produced from anaerobic digestion to an anaerobic level of the lagoon 102.

The invention claimed is:

1. A method of remediating livestock waste comprising:
    establishing a lagoon of effluent, comprising a set of sub-portions at different levels in the lagoon associated with a corresponding set of concentrations of dissolved oxygen, each sub-portion of the lagoon having a different concentration of dissolved oxygen;
    establishing an incubator comprising a set of sub-portions associated with said set of concentrations of dissolved oxygen, each sub-portion of the incubator having a different concentration of dissolved oxygen;
    transmitting a volume of effluent from each sub-portion of the lagoon to a corresponding sub-portion of an incubator having a substantially similar concentration of dissolved oxygen as said sub-portion of the lagoon; and
    generating a first remediated volume of effluent in said corresponding sub-portion of the incubator responsive to proliferating a first microorganism which uses a first compound in said volume of effluent as substrate for growth, the first microorganism enabling a first chemical reaction which alters the first compound.

2. The method of claim 1, further comprising:
    transmitting said first remediated volume of effluent and said first micro-organism from said corresponding sub-portion of the incubator to a corresponding sub-portion of the lagoon having a substantially similar concentration of dissolved oxygen as said corresponding sub-portion of the incubator; and generating a second remediated volume of effluent in said corresponding sub-portion of the lagoon responsive to proliferating said first micro-organism.

3. The method of claim 1, further comprising:

transmitting said first remediated volume of effluent and said first micro-organism from said corresponding sub-portion of the incubator to a corresponding sub-portion of the lagoon having a substantially similar concentration of dissolved oxygen as said corresponding sub-portion of the incubator; and generating a second remediated volume of effluent in the corresponding sub-portion of the lagoon responsive to proliferating a second microorganism which uses a second compound in said first remediated volume of effluent as substrate for growth, said second microorganism enabling a second chemical reaction which alters said second compound.

4. The method of claim 1, wherein said first microorganism is a phosphobacterium and said first compound comprises phosphate.

5. The method of claim 1, wherein said first microorganism is a nitrobacterium and said first compound comprises nitrogen.

6. The method of claim 1, wherein said first microorganism is a sulfbacterium and said first compound comprises sulfur.

7. The method of claim 1, wherein said first microorganism is a hydrocarbon reducing bacterium and said first compound comprises hydrocarbon.

8. The method of claim 1, wherein said set of concentrations of dissolved oxygen comprise concentrations corresponding to a gradient of concentrations ranging from zero to 5 mg/L.

9. The method of claim 8, further comprising:

transmitting a volume of effluent from a sub-portion of the lagoon associated with a dissolved oxygen concentration of substantially zero to a reactor; and generating a second remediated volume of effluent in said reactor responsive to proliferating a second microorganism which uses a second compound in said volume of effluent as substrate for growth, said second microorganism enabling a second chemical reaction which alters said second compound.

10. The method of claim 8, wherein said second microorganism is a thermophilic bacterium.

11. The method of claim 9, wherein said second chemical reaction which alters the second chemical compound produces a gaseous by-product and further comprising:

transmitting the gaseous by-product to a growth tube;

proliferating, in the growth tube, an algae that transforms the gaseous by-product into oxygen.

12. The method of claim 11, further comprising:

transmitting said algae from said growth tube to a sub-portion of the lagoon; and generating an increased dissolved oxygen concentration in said sub-portion of the lagoon responsive to proliferating said algae in said sub-portion of the lagoon.

13. The method of claim 8, wherein said second chemical reaction which alters the second chemical compound produces a gaseous by-product and further comprising:

transmitting said gaseous by-product to a refinery area; and filtering said gaseous by-product in the refinery area to produce methane.

14. The method of claim 8, further comprising:

generating an increased dissolved oxygen concentration in a sub-portion of the lagoon responsive to mechanically aerating said sub-portion of the lagoon.

15. The method of claim 8, further comprising:

generating an increased dissolved oxygen concentration in a sub-portion of the incubator responsive to mechanically aerating said sub-portion of the incubator.

16. The method of claim 1, wherein proliferating said first microorganism in said corresponding sub-portion of the incubator comprises:

agitating said volume of effluent such that the dispersion of the volume of effluent within the corresponding sub-portion of the incubator is maximized and the transmission of the volume of effluent between said set of sub-portions of the incubator is minimized.

* * * * *